US00PP15391P2

(12) United States Plant Patent
Moonen

(10) Patent No.: US PP15,391 P2
(45) Date of Patent: Nov. 30, 2004

(54) ***VERBENA* PLANT NAMED 'KIEVERSTAR SC'**

(50) Latin Name: *Verbena hybrida*
Varietal Denomination: Kieverstar SC

(75) Inventor: Carla Moonen, Enkhuizen (NL)

(73) Assignee: Kieft Seeds Holland, Venhuizen (NL)

( * ) Notice: Subject to any disclaimer, the term of this patent is extended or adjusted under 35 U.S.C. 154(b) by 0 days.

(21) Appl. No.: 10/747,729

(22) Filed: Dec. 29, 2003

(51) Int. Cl.[7] ..... A01H 5/00

(52) U.S. Cl. ..... Plt./308

(58) Field of Search ..... Plt./308

*Primary Examiner*—Bruce R. Campell
*Assistant Examiner*—W C Haas
(74) *Attorney, Agent, or Firm*—C. A. Whealy

(57) ABSTRACT

A new and distinct cultivar of *Verbena* plant named 'Kieverstar SC', characterized by its compact, upright, somewhat outwardly spreading, and mounded plant habit; freely branching habit; dense and bushy growth habit; dark green-colored leaves; and red purple and light pink bi-colored flowers.

1 Drawing Sheet

Botanical classification/cultivar designation: *Verbena hybrida* cultivar Kieverstar SC.

BACKGROUND OF THE INVENTION

The present Invention relates to a new and distinct cultivar of *Verbena* plant, botanically known as *Verbena hybrida*, and hereinafter referred to by the name 'Kieverstar SC'.

The new *Verbena* was discovered by the Inventor in 1999 as a naturally-occurring whole plant mutation of an unnamed *Verbena hybrida* seedling selection, not patented, in a greenhouse in Venhuizen, The Netherlands. The new *Verbena* was selected by the Inventor on the basis of its unique flower color and compact growth habit.

Asexual reproduction of the new cultivar by terminal cuttings taken in a controlled environment in Venhuizen, The Netherlands, since 1999, has shown that the unique features of this new *Verbena* are stable and reproduced true to type in successive generations of asexual reproduction.

SUMMARY OF THE INVENTION

The following traits have been repeatedly observed and are determined to be the unique characteristics of 'Kieverstar SC'. These characteristics in combination distinguish 'Kieverstar SC' as a new and distinct cultivar:

1. Compact, upright, somewhat outwardly spreading, and mounded plant habit.
2. Freely branching habit; dense and bushy growth habit.
3. Dark green-colored leaves.
4. Red purple and light pink bi-colored flowers.

Plants of the new *Verbena* differ primarily from plants of the mutation parent in flower color as plants of the unnamed selection had solid purple-colored flowers.

Plants of the new *Verbena* can be compared to plants of the cultivar Kieverbviviole, not patented. In side-by-side comparisons conducted in Venhuizen, The Netherlands, plants of the new *Verbena* differed primarily from plants of the cultivar Kieverbviviole in flower coloration as plants of the cultivar Kieverbviviole had light purple and violet bi-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photograph differ slightly from the color values cited in the detailed botanical description which accurately describe the colors of the new *Verbena*.

The photograph at the top of the sheet comprises a side perspective view of a typical flowering plant of 'Kieverstar SC' grown in a container.

The photograph at the bottom of the sheet comprises a close-up view of typical inflorescences and leaves of 'Kieverstar SC'.

DETAILED BOTANICAL DESCRIPTION

The cultivar Kieverstar SC has not been observed under all possible environmental conditions. The phenotype may vary somewhat with variations in environment such as temperature and light intensity without, however, any variance in genotype. The aforementioned photographs and following observations and measurements describe plants grown in Lompoc, Calif., under commercial practice during the winter and spring in a polycarbonate-covered greenhouse with day temperatures about 18 to 24° C., night temperatures about 16 to 18° C., and light levels about 4,000 to 8,000 foot-candles. Cuttings were planted in 12.7-cm containers, pinched one time, and grown for about 13 weeks. In the following description, color references are made to The Royal Horticultural Society Colour Chart, 1995 Edition, except where general terms of ordinary dictionary significance are used.

Botanical classification: *Verbena hybrida* cultivar Kieverstar SC.

Parentage: Naturally-occurring whole plant mutation of unnamed *Verbena hybrida* seedling selection, not patented.

Propagation:

*Type cutting.*—Terminal cuttings.

*Time to initiate roots, winter and summer.*—About 12 days at 21° C.

*Time to produce a rooted cutting or liner.*—Summer: About 21 days at 21° C. Winter: About 28 days at 21° C.

*Root description.*—Fine; white in color.

*Rooting habit.*—Freely branching.

Plant description:

*Form.*—Compact, upright, somewhat outwardly spreading, and mounded plant habit.

*Growth and branching habit.*—Moderately vigorous and freely-branching with about 15 to 20 lateral branches developing after pinching; dense and bushy growth habit.

*Plant height.*—About 15 cm.

*Plant diameter or spread.*—About 30 cm.

*Lateral branches.*—Length: About 18 to 20 cm. Diameter: About 3 mm. Internode length: About 4.5 cm. Strength: Strong. Texture: Pubescent. Color: 144C.

*Foliage description.*—Arrangement: Opposite, simple. Length: About 7.5 cm. Width: About 3 cm. Shape: Deltoid. Apex: Acute. Base: Acute to attenuate. Margin: Irregularly crenate. Texture, upper and lower surfaces: Coarse, pubescent. Venation pattern: Pinnate. Color: Young foliage, upper surface: 137C. Young foliage, lower surface: 146C. Fully expanded, upper surface: 147A. Fully expanded, lower surface: 147B. Venation, upper surface: 147C. Venation, lower surface: 144D. Petiole: Length: About 7 mm. Diameter: About 2 mm. Color: 144D.

Flower description:

*Flower type and habit.*—Single upright salverform bi-colored flowers arranged on terminal racemes; flowers sessile. Freely flowering with about 28 flowers and flower buds per raceme; about two racemes per lateral branch. Inflorescences positioned above and beyond the foliage. Flowers last about two to four days under greenhouse conditions. Flowers not persistent.

*Fragrance.*—None detected.

*Flowering season.*—In the garden, flowering is continuous from spring until fall.

*Inflorescence size.*—Diameter: About 5 cm. Height: About 3.4 cm.

*Flower size: Diameter: About* 1.8 cm. Tube length: About 2 cm. Throat diameter: About 2 mm. Tube diameter, at base: About 1.5 to 2 mm.

*Flower buds.*—Rate of opening, from showing color to fully open flower: About 1 to 2 days. Length: About 1.3 cm. Diameter, apex: About 3 mm. Diameter, base: About 2.5 mm. Shape: Tubular. Color: 61A.

*Petals.*—Quantity/arrangement: Five per flower fused at base. Lobe length: About 8 to 10 mm. Lobe width: About 9 mm. Shape: Roughly cordate. Apex: Emarginate. Margin: Entire. Texture, upper and lower surfaces: Velvety, smooth. Color: When opening, upper surface: Towards the center, 61A; towards the margins, 62A. When opening, lower surface: Towards the margins and base, 69A to 69B; towards the apex, 72B. Fully opened, upper surface: Towards the center, 71A to 72B; towards the margins, 62D. Fully opened, lower surface: Towards the center, 72D; towards the margins, 73D. Throat: 144D. Tube: 62D.

*Sepals.*—Quantity/arrangement: Five, fused into a tube. Length: About 1.3 cm. Diameter: About 1 mm. Shape: Ligulate. Apex: Acute. Margin: Entire. Texture, upper and lower surfaces: Coarse, pubescent. Color, upper surface: 143D. Color, lower surface: 143B.

*Peduncles.*—Length: About 5 cm. Diameter: About 2 mm. Angle: Upright to about 45° from vertical. Strength: Strong. Color: 144C.

*Reproductive organs.*—Stamens: Quantity: Four. Anther shape: Ovoid. Anther length: Less than 1 mm. Anther color: 1A. Pollen amount: Scarce. Pollen color: 10B. Pistils: Quantity: One. Pistil length: About 1.8 cm. Stigma shape: Bi-parted. Stigma color: 144D. Style length: About 1.6 cm. Style color: 144D. Ovary color: 144D.

*Fruit/seed.*—Fruit and seed production has not been observed.

Disease/pest resistance: Plants of the new *Verbena* have not been observed to be resistant to pathogens and pests common to *Verbena.*

Temperature tolerance: Plants of the new *Verbena* have been observed to be tolerant to temperatures ranging from 2 to 40° C.

It is claimed:

1. A new and distinct cultivar of *Verbena* plant named 'Kieverstar SC', as illustrated and described.

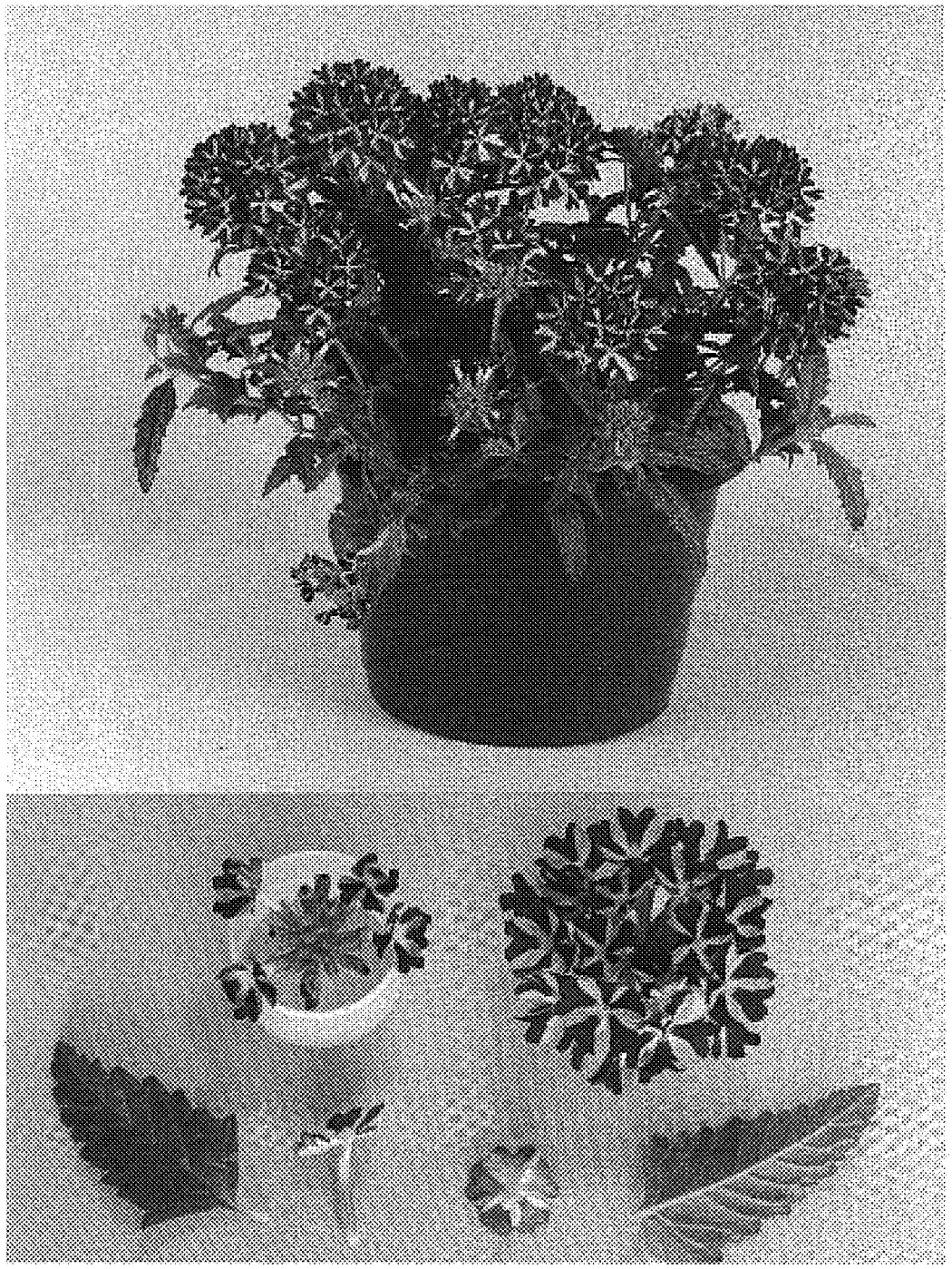

* * * * *